(12) United States Patent
Caswell

(10) Patent No.: US 8,425,944 B2
(45) Date of Patent: *Apr. 23, 2013

(54) FLAVORED COLONIC CLEANSING SYSTEM

(75) Inventor: Michael L. Caswell, Lynchburg, VA (US)

(73) Assignee: C. B. Fleet Company, Inc., Lynchburg, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/184,007

(22) Filed: Jul. 15, 2011

(65) Prior Publication Data

US 2011/0274765 A1 Nov. 10, 2011

Related U.S. Application Data

(63) Continuation of application No. 11/680,819, filed on Mar. 1, 2007, now Pat. No. 7,985,429.

(60) Provisional application No. 60/778,744, filed on Mar. 3, 2006.

(51) Int. Cl.
- *A61K 33/42* (2006.01)
- *A61K 33/00* (2006.01)
- *A61K 31/70* (2006.01)

(52) U.S. Cl.
USPC .............. 424/606; 424/601; 424/722; 514/23

(58) Field of Classification Search .................. None
See application file for complete search history.

(56) References Cited

U.S. PATENT DOCUMENTS

| | | | |
|---|---|---|---|
| H859 H | 12/1990 | Augustine |
| 5,013,716 A | 5/1991 | Cherukuri et al. |
| 5,106,632 A | 4/1992 | Wong et al. |
| 5,124,144 A | 6/1992 | Giorgetti et al. |
| 5,274,001 A | 12/1993 | Borody |
| 5,498,425 A | 3/1996 | Wood et al. |
| 5,616,346 A | 4/1997 | Aronchick |
| 5,688,529 A | 11/1997 | Lidgate et al. |
| 5,997,906 A | 12/1999 | Wood et al. |
| 6,103,268 A | 8/2000 | Borody et al. |
| 6,156,332 A | 12/2000 | Bakal et al. |
| 6,162,464 A | 12/2000 | Jacob et al. |
| 6,361,799 B1 | 3/2002 | Palkhiwala |
| 6,737,068 B2 | 5/2004 | Durden |
| 6,806,256 B2 | 10/2004 | Ulrich et al. |
| 6,866,873 B2 | 3/2005 | Stern |
| 6,906,038 B2 | 6/2005 | Mazer |
| 6,946,149 B2 | 9/2005 | Cleveland |
| 7,101,572 B2 | 9/2006 | Santos et al. |
| 7,169,381 B2 | 1/2007 | Barras et al. |
| 7,332,184 B2 | 2/2008 | Vanner et al. |
| 7,867,521 B2 | 1/2011 | Ayala et al. |
| 7,985,429 B2 | 7/2011 | Caswell |
| 7,998,510 B2 | 8/2011 | Caswell |
| 8,129,430 B2 | 3/2012 | Caswell et al. |
| 8,263,136 B2 | 9/2012 | Caswell |
| 2002/0137803 A1 | 9/2002 | Kirkland |
| 2004/0071779 A1 | 4/2004 | Keiser et al. |
| 2004/0101491 A1 | 5/2004 | Stier |
| 2004/0115282 A1 | 6/2004 | Keiser et al. |
| 2004/0143005 A1 | 7/2004 | Barras et al. |
| 2004/0170698 A1 | 9/2004 | Halow |
| 2004/0192614 A1 | 9/2004 | Vanner et al. |
| 2005/0061861 A1 | 3/2005 | Pennino |
| 2005/0152989 A1 | 7/2005 | Pelham et al. |
| 2005/0271749 A1 | 12/2005 | Borody et al. |
| 2006/0051428 A1 | 3/2006 | Ayala et al. |
| 2007/0082061 A1 | 4/2007 | Ayala et al. |
| 2007/0207216 A1 | 9/2007 | Caswell |
| 2008/0044489 A1 | 2/2008 | Caswell |
| 2008/0145445 A1 | 6/2008 | Ayala et al. |
| 2011/0308988 A1 | 12/2011 | Caswell |
| 2013/0039994 A1 | 2/2013 | Caswell |

FOREIGN PATENT DOCUMENTS

| | | |
|---|---|---|
| BE | 541665 | 8/1959 |
| EP | 0396165 | 11/1990 |
| WO | WO 88/03762 | 6/1988 |
| WO | WO89/05659 | 6/1989 |
| WO | WO 93/17589 | 9/1993 |
| WO | WO 94/12191 | 6/1994 |
| WO | WO 98/26776 | 6/1998 |
| WO | WO 98/43654 | 10/1998 |
| WO | WO 2004/032926 | 4/2004 |
| WO | WO 2004/037292 | 5/2004 |
| WO | WO 2006/028632 | 3/2006 |
| WO | WO 2006/118562 | 11/2006 |
| WO | WO 2007/022435 | 2/2007 |
| WO | WO 2007/044681 | 4/2007 |

OTHER PUBLICATIONS

Verghese, V.J. et al., "Low-salt Bowel Cleansing Preparation (LoSo Prep) as Preparation for Colonoscopy: A Pilot Study", Aliment Pharmacol Ther, vol. 16, pp. 1327-1331, (2002).
Reddy, D. et al., "Efficacy and Safety of Oral Sodium Phosphate Versus Polyethylene Glycol Solution for Bowel Preparation for Colonoscopy", Indian Journal of Gastroenterology, vol. 21, pp. 219-221, (2002).
Martinek, J. et al., "Preparation of the Gut Before Colonoscopy", Prakt., vol. 82, pp. 472-476, (2002). (original and translated version).
Web Page: Wild Resolver, Obtained from: www.wild.de/wild/opencms/en/innovation/technology/wild_innovation_technology_resolver.html, p. 1, Printed: Aug. 20, 2004.
Web Page: Crystal Light Product Information, Obtained from: www.kraftfoods.com/crystallight/cl_products.html, pp. 1-2, Printed: Feb. 17, 2004.
Web Page: Kraft Food Products, Pink Lemonade, Obtained from: www.kraftfoods.com/knet_print_version.aspx?s=product&m=product/product_display&Product=4300095019&print_show=1&U3=****4300095019*, p. 1, Printed: May 19, 2004.
Web Page: Kraft Food Products, Lemonade, Obtained from: www.kraftfoods.com/knet_print_version.aspx?s=product&m=product/product_display&Product=4300095023&print_show=1&U3=****4300095023*, p. 1, Printed: May 19, 2004.

(Continued)

*Primary Examiner* — James H. Alstrum-Acevedo
*Assistant Examiner* — Frank Choi
(74) *Attorney, Agent, or Firm* — Evan Law Group LLC

(57) ABSTRACT

A kit for colonic cleansing includes a phosphate salt laxative, a flavorant, and an oral rehydration mixture. The flavorant includes aspartame and a citrate, and the oral rehydration mixture includes sodium and a glucose containing saccharide. The kit may be used for a colonic cleansing procedure by combining the phosphate salt laxative and the flavorant to provide a flavored laxative liquid, orally administering to a subject the flavored laxative liquid, and orally administering to the subject an oral rehydration liquid.

17 Claims, 5 Drawing Sheets

OTHER PUBLICATIONS

Web Page: Kraft Food Products, Sunrise Classic Orange, Obtained from: www.kraftfoods.com/knet_print_version.aspx?s=product&m=product/product_display&Product=4300094541&U3=****4300094541*, p. 1, Printed: May 18, 2004.

Web Page: Kraft Food Products,Tangerine Strawberry, Obtained from: www.kraftfoods.com/knet_print_version.aspx?s=product&m=product/product_display&Product=4300095024&U3=****4300095024*, p. 1, Printed: May 19, 2004.

Web Page: Kraft Food Products, Rasberry Ice, Obtained from: www.kraftfoods.com/knet_print_version.aspx?s=product&m=product/product_display&Product=4300095028&print_show=1&U3=****4300095028*, p. 1, Printed: May 19, 2004.

Web Page: Kraft Food Products, Rasberry Peach, Obtained from: www.kraftfoods.com/knet_print_version.aspx?s=product&m=product/product_display&Product=4300095026&print_show=1&U3=****4300095026*, p. 1, Printed: May 19, 2004.

Anonymous, "Product Information—Crystal Light Iced Tea Decaffeinated Sugar Free"., www.kraftfoods.com/main.aspx?s=product&m=product/Product_display&Site=1&Product=4300095016, p. 1, Printed: Dec. 2, 2005.

Anonymous, "Product Information—Jell-O Gelatin Dessert Orange 0 carb Sugar Free 10.2g"., www.greatlowcarb.com/product.php?p=4085?w=100>.,pp. 1-2, Printed: Dec. 2, 2005.

International Search Report and Written Opinion dated Jan. 11, 2006 for corresponding PCT application No. PCT/US2005/028132.

Web Page: Crystal Light-Lemonade-Pink Lemonade Sugar Free Product Information, Obtained from: www.kraftfoods.com/knet_print_version.aspx?s=product&m=product/product_display&Product=4300095019&print_show=1, 1 page, printed Apr. 30, 2007.

Web Page: Crystal Light-Lemonade-Raspberry Lemonade Sugar Free Product Information, Obtained from: www.kraftfoods.com/knet_print_version.aspx?s=product&m=product/product_display&Product=4300094963&print_show=1, 1 page, printed Apr. 30, 2007.

Web Page: Crystal Light-Fruit Drinks-Strawberry-Kiwi Sugar Free Product Information, Obtained from: www.kraftfoods.com/knet_print_version.aspx?s=product&m=product/product_display&Product=4300095008&print_show=1, 1 page, printed Apr. 30, 2007.

Web Page: Crystal Light-Fruit Drinks-Strawberry-Orange-Banana Sugar Free Product Information, Obtained from: www.kraftfoods.com/knet_print_version.aspx?s=product&m=product/product_display&Product=4300095009&print_show=1, 1 page, printed Apr. 30, 2007.

Web Page: Crystal Light-Fruit Drinks-Pineapple-Orange Sugar Free Product Information, Obtained from: www.kraftfoods.com/knet_print_version.aspx?s=product&m=product/product_display&Product=4300095022&print_show=1, 1 page, printed Apr. 30, 2007.

Web Page: Crystal Light-Sunrise-Sunrise Ruby Red Grapefruit Product Information, Obtained from: www.kraftfoods.com/knet_print_version.aspx?s=product&m=product/product_display&Product=4300097199&print_show=1, 1 page, printed Apr. 30, 2007.

Anal itching [online] retrieved on Nov. 5, 2006; retrieved from the Internet [www.cnn.com/HEALTH/library/DS/00453.html]; pp. 1-4, May 5, 2006.

Met-Rx Berry Drink Data sheet online [retrieved Mar. 21, 2002]www.physicallyelite.com/store/store.cfm?do=detail&product_id=12384, pp. 1-5.

Ingredient list for EAS Myoplex original nutrition shake, (2000).

Myoplex datasheet online [retrieved Nov. 10, 2000] http://eas.com/index.asp, Myoplex pp. 1-2.

Rao, "Toxicologic Pathology of the Kidney and Urinary Bladder," Toxicologic Pathology, vol. 30, No. 6, pp. 651-656, 2002.

Vanner et al., "A Randomized Prospective Trial Comparing Oral Sodium Phosphate with Standard Polyethylene Glycol-Based Lavage Solution (Golytely) in the Preparation of Patients for Colonoscopy," The American Journal of Gastroenterology, vol. 85, No. 4, pp. 422-427, 1990.

Toblli et al., "Potassium citrate administration ameliorates tubulointerstitial lesions in rats with uric acid nephropathy," Clinical Nephrology, vol. 55, No. 1, pp. 59-68, 2001.

Lacour et al., "Effet du citrate et des phosphate sur le transport du calcium dans l'iléon de rat in vitro," Gastroenterol Clin. Biol., 18, pp. 938-944, 1994. (Summary in English).

Oikawa et al., "Modulation of plasminogen activator inhibitor-1 in vivo : A new mechanism for the anti-fibrotic effect of rennin-angiotensin inhibition," Kidney International, vol. 51, pp. 164-172, 1997.

Marangella et al., "Crystallization Inhibitors in the Pathophysiology and Treatment of Nephrolithiasis," Urologia Int., 72, Suppl. 1, pp. 6-10, 2004.

Neuhofer et al., "Chronic COX-2 inhibition reduces medullary HSP70 expression and induces papillary apoptosis in dehydrated rats," Kidney International, vol. 65, pp. 431-441, 2004.

Ma et al., "Model of robust induction of glomerulosclerosis in mice: Importance of genetic background," Kidney International, vol. 64, pp. 350-355, 2003.

Smoyer et al., "Ischemic Acute Renal Failure Induces Differential Expression of Small Heat Shock Proteins," J. Am Soc Nephrol, 11, pp. 211-221, 2000.

Desmeules et al., "Acute Phosphate Nephropathy and Renal Failure," NEJM, 349, pp. 1006-1007, 2003.

Markowitz et al., "Acute Phosphate Nephropathy following Oral Sodium Phosphate Bowel Purgative: An Underrecognized Cause of Chronic Renal Failure," J Am Soc Nephrol, 16, pp. 3389-3396, 2005.

Markowitz et al., "Renal Failure Due to Acute Nephrocalcinosis Following Oral Sodium Phosphate Bowel Cleansing," Human Pathology, 35, 675-684, 13 pages total, 2004.

Ritskes-Hoitinga et al., "Phosphorus-Induced Nephrocalcinosis and Kidney Function in Female Rats," J. Nutr., 119, pp. 1423-1431, 1989.

Orias et al., "Extreme Hyperphosphatemia and Acute Renal Failure after a Phosphorus-Containing Bowel Regimen," Am J Nephrol, 19, pp. 60-63, (1999).

Fine et al., "Severe Hyperphosphatemia Following Phosphate Administration for Bowel Preparation in Patients With Renal Failure: Two Cases and a Review of the Literature," American Journal of Kidney Diseases, vol. 29, No. 1, pp. 103-105, (1997).

Wangoo et al., "Chronobiology of urinary citrate excretion amongst stone-fomers and healthy males from North Western India", Urological Research, 19:203-206, (1991).

Moeckel et al, "Distribution of de novo synthesized betaine in rat kidney: role of renal synthesis on medullary betaine accumulation," Am. J. Physiol., 272, pp. F94-F99, (1997).

Moeckel et al, "COX2 Activity Promotes Organic Osmolyte Accumulation and Adaptation of Renal Medullary Interstitial Cells to Hypertonic Stress," Journal of Biological Chemistry, vol. 278, No. 21, pp. 19352-19357, (2003).

Moeckel et al., "Role of integrin $\alpha_1\beta_1$ in the regulation of renal medullary osmolyte concentration," Am J Physiol Renal Physiol, 290, pp. F223-F231, (2006).

Marshall et al., "Prospective, randomized trial comparing sodium phosphate solution with polyethylene glycol-electrolyte electrolyte lavage for colonoscopy preparation," Gastrointestinal Endoscopy, vol. 39, No. 5, pp. 631-634, (1993).

Petsite.com Ltd., "Amazing Rodent Facts," located at http://www.petalia.com.au/templates/StoryTemplate_Process.cfm?Story_No=350, p. 1, printed Nov. 2007.

Nie et al., "Distinct Contributions of T1R2 and T1R3 Taste Receptor Subunits to the Detection of Sweet Stimuli," Current Biology, vol. 15, pp. 1948-1952, (2005).

International Food Information Council Foundation, "Everything You Need to Know About Sucralose," 2 pages, (1998).

International Food Information Council Foundation, "Everything You Need to Know About Acesulfame Potassium," 2 pages, (1998).

Calorie Control Council, "Low-Calorie Sweeteners: Acesulfame Potassium," can be found at http://www.caloriecontrol.org/acesluf.html, 3 pages, (2004).

International Food Information Council Foundation, "Low-Calorie Sweeteners: Adding Reduced-Calorie Delights to a Healthful Diet," can be found at http://www.ific.org/foodinsight/1998/jf/lcsfi198.cfm?renderforprint=1, 4 pages, (1998).

International Food Information Council Foundation, "More Choices for the Sweet Life," can be found at http://www.ific.org/foodinsight/2002/so/morechoicesfi502.cfm?renderforprint=1, 3 pages, (2002).

FoodProductionDaily.com/Europe, "Sweet taste study promises perfect sugar replacement," can be found at http://www.foodproductiondaily.com/news/printNewsBis.asp?id=63743, 2 pages, (2005).

International Search Report dated Mar. 29, 2007 for application No. PCT/US2006/039419.

Khashab, M. et al., "Efficacy and tolerability of a new formulation of sodium phosphate tablets (INKP-101), and a reduced sodium phosphate dose, in colon cleansing: a single-center open-label pilot trial", Aliment Pharmacol Ther., vol. 21, pp. 465-468, (2005).

Rex, D.K. et al., "Safety and efficacy of two reduced dosing regimens of sodium phosphate tablets for preparation prior to colonoscopy", Aliment Pharmacol Ther., vol. 16, pp. 937-944, (2002).

Salix Pharmaceuticals, Inc., "Visicol® Product Information", http://www.salix.com/products_visicol.aspx, 1 page, printed on Aug. 16, 2006.

InKine Pharmaceutical Company, Inc., "INKP-102 Tablet Posters; A new purgative from InKine Pharmaceutical Company, Inc., a subsidiary of Salix Pharmaceuticals", American College of Gastroenterology, Annual Scientific Meeting, 28 pages, Oct. 30-Nov. 2, 2005.

Gatorade Sports Science Institute, "Roundtable; Intestinal fluid absorption in exercise and disease", SSE Roundtable #11, found at http://gssiweb.com/Article_Detail.aspx?articleid=50&level=4&topic=5, vol. 4, No. 1, 5 pages, (1993), (2002).

McNaught, A.D. "Nomenclature of carbohydrates; recommendations 1996", Pure & Applied Chemistry, vol. 68, No. 10, pp. 1919-2008, (1996).

Gatorade Beverage Comparison Chart, http://www.gssiweb.com/pdf/gatorade_bev_chart.pdf#search=%22gatorade%20beverage%20comparison%20chart%22, 2 pages, printed Sep. 2005.

Sports Drink Comparisons, The University of Arizona, Group 14, Honors Biology 181, Fall 1998, found at http://student.biology.arizona.edu/honors98/group14/sportsdrinks.html, 2 pages, printed on Feb. 25, 2008.

Accelerade, "Sports Drink Comparison", PacificHealth Laboratories, Inc., found at http://www.accelerade.com/pages/product_compare.html, 1 page, printed on Sep. 29, 2005.

All-Sport Body Quencher, "Product Comparison", found at http://www.drinkallsport.com/pop/product_compare.htm, 1 page, printed on Sep. 29, 2005.

Afridi, S.A. et al., "Prospective, randomized trial comparing a new sodium phosphate-bisacodyl regimen with conventional PEG-ES lavage for outpatient colonoscopy preparation," Gastrointestinal Endoscopy, pp. 485-489, vol. 41, (1995).

Arezzo, A. "Prospective randomized trial comparing bowel cleaning preparations for colonoscopy," Surgical Laparoscopy: Endoscopy & Percutaneous Techniques, pp. 215-217, vol. 10, No. 4, (2000).

Aronchick, C.A. et al., "A novel tableted purgative for colonoscopic preparation: efficacy and safety comparisons with Colyte and Fleet Phospho-Soda," Gastrointestinal Endoscopy, pp. 346-352, vol. 52, No. 3, (2000).

Avery, M.E. et al., "Oral therapy for acute diarrhea: The underused simple solution," The New England Journal of Medicine, pp. 891-894, vol. 323, No. 13, (1990).

Barclay, R.L. et al., "Carbohydrate-electrolyte rehydration protects against intravascular volume contraction during colonic cleansing with orally administered sodium phosphate", Gastrointestinal Endoscopy, pp. 633-638, vol. 56, No. 5, (2002).

Bawani, M. et al., "A Single Blinded, Prospectively Randomized Comparison of Oral Phosphosoda (OP) with Polyethylene Glycol Based Solution (PG) as a Colonic Lavage for Colonoscopy," Am. J. Gastroent., p. 1350, vol. 86, Abstract 239, (1991).

Bawani, M.H. et al., "A Single Blind Control Study of Fleet Oral Phosphosoda Laxative and Magnesium Citrate for Colonoscopy Preparation," AJG, p. 1964, vol. 91, Abstract 316, (1996).

Berkelhammer, C. et al., "Low-Volume Oral Colonoscopy Bowel Preparation: Sodium Phosphate and Magnesium Citrate," Gastrointestinal Endoscopy, pp. 89-94, vol. 56, No. 1, (2002).

Bujnada, L. et al., "Tolerance and Colon Cleansing with Two Preparations. Polyethylene Glycol Versus Sodium Phosphate," Gastroenterologia Y. Hepatologia, pp. 9-12, vol. 24, (2001).

Chaleoykitti, B., "Comparative Study Between Polyethylene Glycol and Sodium Phosphate Solution in Elective Colorectal Surgery," J. Med. Assoc. Thai, pp. 92-96, vol. 85, (2002).

Chan, A. et al., "Use of Oral Sodium Phosphate Colonic Lavage Solution by Canadian Colonoscopists: Pitfalls and Complications," Can J. Gastroenterol., pp. 334-338, vol. 11, No. 4, (1997).

Chia, Y.W. et al., "Role of Oral Sodium Phosphate and Its Effectiveness in Large Bowel Preparation for Out-Patient Colonoscopy," J.R. Coll. Surg. Edinb., pp. 374-376, vol. 40, (1995).

Chilton, A.P. et al., "A Blinded, Randomized Comparison of a Novel, Low-Dose, Triple Regimen with Fleet Phospho-Soda: A Study of Colon Cleanliness, Speed and Success of Colonoscopy," Endoscopy, pp. 37-41, vol. 32, No. 1, (2000).

Clarkston, W.K. et al., "Oral sodium phosphate versus sulfate-free polyethylene glycol electrolyte lavage solution in outpatient preparation for colonoscopy: a prospective comparison," Gastrointest. Endosc., pp. 42-48, vol. 43, (1996).

Cohen, S.M. et al., "Prospective, randomized, endoscopic-blinded trial comparing precolonoscopy bowel cleansing methods," Dis. Colon Rectum, pp. 689-696, vol. 37, (1994).

Da Silva, M.M. et al., "Colonoscopy preparation in children: safety, efficacy, and tolerance of high- versus low-volume cleansing methods," Journal of Pediatric Gastroenterology and Nutrition, pp. 33-37, vol. 24, (1997).

Del Piano, M. et al., "A comparison of 3 methods of preparation for colonoscopy," Minerva Gastroenterol. Dietol, pp. 89-92, vol. 39, (1993).

Fernandez, J.M.P. et al., "Characterization of the safety, effectiveness and use of oral sodium phosphate," Revista Espanola De Enferm. Digestives, pp. 220-225, vol. 93, No. 4, (2001).

Frommer, D. "Cleansing ability and tolerance of three bowel preparation for colonoscopy," Dis. Colon Rectum, pp. 100-104, vol. 40, (1997).

Golub, R.W. et al., "Colonoscopic Bowel Preparations—Which One?," Dis. Colon. Rectum., pp. 594-599, vol. 38, (1995).

Greenleaf, J.E. et al., "Plasma volume expansion with oral fluids in hypohydrated men at rest and during exercise," Aviat Space Environ. Med., pp. 837-844, vol. 69, (1998).

Gremse, D.A. et al., "Comparison of oral sodium phosphate to polyethylene glycol-based solution for bowel preparation for colonoscopy in children," J. Ped. Gast. And Nutrition, pp. 586-590, vol. 23, (1996).

Habr-Gama, A., "Bowel preparation for colonoscopy: comparison of mannitol and sodium phosphate: results of a prospective randomized study," Rev. Hosp. Clin. Fac. Med. S. Paulo, pp. 187-192, vol. 54, No. 6, (1999).

Handelsman, J.C. et al., "Experience with ambulatory preoperative bowel preparation at the Johns Hopkins hospital," Arch. Surg., pp. 441-444, vol. 128, (1993).

Haroon, et al., "A randomized clinical trial comparing oral sodium phosphate (NaP) with standard polyethylene glycol-based lavage solution (Colyte) in the preparation of patients for colonoscopy," Gastroenterology, vol. 102, No. 4, Abstract No. 2112, (1992).

Henderson, J.M. et al., "Single-day, divided-dose oral sodium phosphate laxative versus intestinal lavage as preparation for colonoscopy: efficacy and patient tolerance," Gastrointest. Endoscopy, pp. 238-243, vol. 42, No. 3, (1995).

Hookey, L.C. et al., "The safety profile of oral sodium phosphate for colonic cleansing before colonoscopy in adults", Gastrointest. Endoscopy, vol. 56, No. 6, pp. 895-902, (2002).

Huynh, T. et al., "Safety profile of 5-h oral sodium phosphate regimen for colonoscopy cleansing: lack of clinically significant hypocalcemia or hypovolemia," Am. J. Gastroenterol., pp. 104-107, vol. 90, (1995).

Johnson, D.R. et al., "Dehydration and orthostatic vital signs in women with hyperemesis gravidarum" Acad. Emerg. Med., pp. 692-697, (7 pages including correction), vol. 2, (1995).

Kim, M. et al., "Patient compliance and satisfaction with oral bowel preparation for outpatient colonoscopy: a prospective, randomized, blinded trial," Dis. Colon Rectum, vol. 40, pp. A42, Abstract No. P48, (1997).

Klein, S. et al., "Enteral and parenteral nutrition," Sleisenger and Fordtran's Gastrointestinal and Liver Disease, pp. 254-277, (1998).

Kolts, B.E. et al., "A comparison of the effectiveness and patient tolerance of oral sodium phosphate, castor oil, and standard electrolyte lavage for colonoscopy or sigmoidoscopy preparation," Am. J. Gastroenterol., pp. 1218-1223, vol. 88, No. 8, (1993).

Kuchel, G.A. et al., "Cardiovascular responses to phlebotomy and sitting in middle-aged and elderly subjects," Arch. Int. Med., pp. 366-370, vol. 152, (1992).

Lapalus, M-G. et al., "Prospective randomized single-blind trial comparing oral sodium phosphate and polyethylene glycol based solution for colonoscopy preparation," Gastroenterol. Clin. Biol., pp. 29-34, vol. 25, (2001).

Lee, J. et al., "A prospective randomised study comparing polyethylene glycol and sodium phosphate bowel cleansing solutions for colonoscopy," The Ulster Medical Journal, pp. 68-72, vol. 68, No. 2, (1999).

McGee, S.R., "Physical examination of venous pressure: a critical review," Am. Heart J., pp. 10-18, vol. 136, (1998).

Macari, M. et al., "Effect of different bowel preparations on residual fluid at CT colonography," Radiology, pp. 274-277, vol. 218, (2001).

Macleod, A.J.M. et al., "A comparison of fleet phospho-soda with picolax in the preparation of the colon for double contrast barium enema," Clinical Radiology, pp. 612-614, vol. 53, (1998).

Marshall, J.B. et al., "Short report: prospective, randomized trial comparing a single dose sodium phosphate regimen with PEG-electrolyte lavage for colonoscopy preparation," Aliment Pharmacol. Ther., pp. 679-682, vol. 7, (1993).

Marshall, J.B. et al., "Prospective, randomized trial comparing sodium phosphate solution with polyethylene glycol-electrolyte lavage for colonoscopy preparation," Gastrointest. Endosc., pp. 631-634, vol. 39, No. 5, (1993).

Martinek, J. et al., "Cisapride does not improve precolonoscopy bowel preparation with either sodium phosphate or polyethylene glycol electrolyte lavage," Gastrointest. Endoscopy, pp. 180-185, vol. 54, No. 2, (2001).

Maughan, R.J. et al., "Post-exercise rehydration in man: effects of electrolyte addition to ingested fluids," Eur. J. Appl. Physiol. Occup. Physiol., pp. 209-215, vol. 69, (1994).

O'Donovan, A.N. et al., "A prospective blinded randomized trial comparing oral sodium phosphate and polyethylene glycol solutions for bowel preparation prior to barium enema," Clin. Radiology, pp. 791-793, vol. 52, (1997).

Oliveria, L.C.C. et al., "Mechanical bowel preparation for elective colorectal surgery; a prospective, randomized, surgeon-blinded trial comparing sodium phosphate and polyethylene glycol-based oral lavage solutions," Dis. Colon Rectum, pp. 585-591, vol. 40, (1997).

Poon, C.M. et al., "Two liters of polyethylene glycol-electrolyte lavage solution versus sodium phosphate as bowel cleansing regimen for colonoscopy: a prospective randomized controlled trial," Endoscopy, pp. 560-563, vol. 34, (2002).

Rex, D.K. et al., "Impact of bowel preparation on efficacy and cost of colonoscopy," Am. J. Gastroenterology, pp. 1696-1700, vol. 97, No. 7, (2002).

Shaoul, R. et al., "Symptoms of hyperphosphatemia, hypocalcemia, and hypomagnesemia in an adolescent after the oral administration of sodium phosphate in preparation for a colonoscopy," Gastrointest. Endosc., pp. 650-652, vol. 53, No. 6, (2001).

Sudduth, R.N. et al., "The effectiveness of simethicone in improving visibility during colonoscopy when given with a sodium phosphate solution: a double-blind randomized study," Gastrointest. Endoscopy, pp. 413-415, vol. 42, No. 5, (1995).

Thomson, A. et al., "Bowel preparation for colonoscopy: a randomized prospective trial comparing sodium phosphate and polyethylene glycol in a predominantly elderly population," J. Gast. and Hepatology, pp. 103-107, vol. 11, (1996).

Unal, S. et al., "A randomized prospective trial comparing 45 and 90-ml oral sodium phosphate with X-Prep in the preparation of patients for colonoscopy," Acta. Gastro-Enterol. Belg., pp. 281-284, vol. 61, (1998).

Wolff, B.G. et al., "A new bowel preparation for elective colon and rectal surgery: a prospective, randomized clinical trial," Arch. Surg., pp. 895-900, vol. 123, (1998).

Yoshioka, K. et al., "Randomized trial of oral sodium phosphate (picolax) for elective colorectal surgery and colonoscopy," Dig. Surg., pp. 66-70, vol. 17, (2000).

Young, C.J. et al., "Oral sodium phosphate solution is a superior colonoscopy preparation to polyethylene glycol with bisacodyl," Dis. Colon Rectum, pp. 1568-1571, vol. 43, (2000).

Tjandra, J. et al., "Carbohydrate-Electrolyte (E-Lyte®) Solution Enhances Bowel Preparation With Oral Fleet® Phospho-soda®", Dis Colon Rectum, 47, pp. 1181-1186, (2004).

Canard, J. et al., "Fleet® Phospho Soda: for Greater Acceptability of the Colic Preparation Before Colonoscopy. Randomized Comparative Single Blind Study Versus Polyethylene Glycol." Acta. Endoscopica, pp. 703-708, vol. 31, (2001).

Translation of the Canard, J., et al reference, (2008).

Oliveira, L. et al., "Mechanical Bowel Preparation With Oral Sodium Phosphate Solution for Colonoscopy. A New Small Volume Solution Compared to the Traditional Mannitol.", Revista do Colegio Brasileiro de Cirurgioes, pp. 353-358, vol. 26, (1999).

Translation of the Oliveira, L. et al reference, (2008).

Salix Pharmaceuticals, Inc., Visicol® Tablets Product Information, 2 pages, (2005).

Isbrucker, R.A. et al., "Risk and safety assessment on the consumption of licorice root (*Glycyrrhiza* sp.), its extract and powder as a food ingredient, with emphasis on the pharmacology and toxicology of glycyrrhizin", Regulatory Toxicology and Pharmacology, vol. 46, pp. 167-192, (2006).

Translation of the Belgium Patent BE 541665 dated Aug. 1959.

Unger et al., "Willingness to Undergo Split-Dose Bowel Preparation for Colonoscopy and Compliance with Split-Dose Instructions," Dig Dis Sci, pp. 2030-2034, (2010).

Balaban, D.H. et al., "Comparison of two dosing regimens of liquid sodium phosphate against a low dose PEG regimen", American Journal of Gastroenterology, vol. 100, No. 9 supplement, pp. S354-S355, (2005).

Food and Drug Administration, "Guidance for Industry: Container closure systems for packaging human drugs and biologics", U.S. Department of Health and Human Services, pp. 1-56, (1999).

Rex, D.K. et al., "Updated recommendations on the safe and effective use of oral sodium phosphates solution" Fleet, found at www.fleetlabs.com/notices/UpdatedRecommendationsOSPS.pdf, pp. 1-10, printed on Jan. 13, 2012, (2007).

DiPalma, J.A. et al., "Biochemical effects of oral sodium phosphate", Digestive Diseases and Sciences, vol. 41, No. 4, pp. 749-753, (1996).

Ainley, E.J. et al., "Measurement of serum electrolytes and phosphate after sodium phosphate colonoscopy bowel preparation: an evaluation", Digestive Diseases and Sciences, vol. 50, No. 7, pp. 1319-1323, (2005).

Malik, P. et al., "Randomized study comparing two refimens of oral sodium phosphates solution versus low-dose polyethylene glycol and bisacodyl", Digestive Diseases and Sciences, vol. 54, No. 4, pp. 833-841, published online Aug. 19, 2008, (2009).

International Search Report dated Dec. 4, 2008 for PCT Application No. PCT/US08/073855.

Gimenez, L., et al., "Prevention of phosphate-induced progression of uremia in rats by 3-phosphocitric acid", Kidney International, vol. 22, pp. 36-41, (1982).

Zechner, V. O., et al., "The Conservative treatment of phosphate calculi with citrate buffer", Wiener Klinische Wochenschrift, vol. 87, No. 9, pp. 300-303, (1975).

Abuelo, J.G. "Normotensive ischemic acute renal failure", New England Journal of Medicine, vol. 357, pp. 797-805, (2007).

Physicians Desk Reference, 58th Edition, pp. 1286-1287, (2004).

Tuorila, H. et al., "Recalling taste intensities in sweetened and salted liquids", Chemical Senses, vol. 21, issue 1, pp. 29-34, (1996).

Mojet, J. et al., "Taste perception with age: Generic or specific losses in supra-threshold intensities of five taste qualities?", Chemical Senses, vol. 28, pp. 397-413, (2003).

Heinzerling, C.I. et al., "Individually modified saliva delivery changes the perceived intensity of saltiness and sourness", Chemosensory Perception, vol. 4, issue 4, pp. 145-153, (2011).

Busch, J.L.H.C. et al., "Temporal contrast of salt delivery in mouth increases salt perception", Chemical Senses, vol. 34, issue 4, pp. 341-348, (2009).

Hayes, J.E. et al., "Explaining variability in sodium intake through oral sensory phenotype, salt sensation and liking", Physiology & Behavior, vol. 100, pp. 369-380, (2010).

FLAVORED COLONIC CLEANSING SYSTEM

REFERENCE TO RELATED APPLICATIONS

This application is a continuation application of U.S. application Ser. No. 11/680,819, filed Mar. 1, 2007, now U.S. Pat. No. 7,985,429, which claims the benefit of U.S. Provisional Application No. 60/778,744 entitled "FLAVORED COLONIC CLEANSING SYSTEM" filed Mar. 3, 2006, which is incorporated by references in its entirety.

BACKGROUND

Colonoscopy screening coupled with polyp removal (polypectomy) significantly reduces the incidence of colorectal carcinoma. Prior to colonoscopy, including virtual colonoscopy procedures, the colon must be cleansed so the surgeon may see any polyps that exist on the interior wall of the colon. The colon also must be cleansed before radiological or surgical procedures involving the colon. This cleansing generally entails the drinking of one or more laxative mixtures.

Aqueous mixtures of sodium phosphate salts (monobasic and dibasic sodium phosphate), such as FLEET® PHOSPHO-SODA®, are very effective oral laxatives and are extensively used prior to colonoscopy, radiological procedures, and surgery. For pre-colonoscopy use, a split regimen is often preferred that includes one 45 mL dose given the evening before colonoscopy and a second 45 mL dose given at least three hours prior to the procedure on the following morning. In order to maintain adequate hydration a large amount of liquids, 3 to 4 liters (L) for example, should be consumed in addition to phosphate salt laxative. These additional liquids may include oral rehydration liquid, which includes sodium and a glucose containing saccharide. U.S. Patent Application Publication No. 2004/0192614 A1 discloses that oral rehydration liquids, in addition to attenuating hypovolemia associated with laxative ingestion, may also result in superior colonic cleansing.

Unfortunately, of the 147,500 new cases of colorectal carcinoma diagnosed in 2003, the American Cancer Society estimates that only 37% of these cases were diagnosed early enough for treatment to offer the best possible prognosis. In addition, colonoscopy screening should be repeated more frequently for subjects who have previously undergone a polypectomy due to their increased risk of recurrent polyp formation. However, in a follow-up phase of the National Polyp Study, at least 20% of subjects who had previously undergone polypectomies failed to return for their follow-up screening. In a more recent study, where 8,865 subjects who had previously undergone a polypectomy underwent a second colonoscopy screening, 2,704 (30.5%) were diagnosed with recurrent polyps. A statistical analysis based on the data from this report projected that 50% of subjects will have recurrent polyps within 7.6 years. Despite this level of risk, many subjects do not undergo additional screening.

One of the main reasons subjects cite for avoiding colonoscopy re-screening is the unpleasant taste of these phosphate based laxative mixtures. Depending on the study, from 15 to 51% of the subjects report discomfort in the form of nausea and vomiting. The extremely salty taste of the laxative mixture is believed to be the cause of this discomfort. Frequently, subjects cannot tolerate the ingestion of the complete initial dose of the preparation, which often prevents them from consuming more than a small portion of the second dose.

SUMMARY

In one aspect, the invention provides a kit for colonic cleansing including a phosphate salt laxative; a flavorant, including aspartame and a citrate; and an oral rehydration mixture, including sodium and a glucose containing saccharide.

In another aspect, the invention provides a kit for colonic cleansing including at least two bottles, each containing from 10 to 75 mL a phosphate salt laxative including water, from 0.05 to 1.5 gram/mL of monobasic sodium phosphate, and from 0.02 to 0.6 gram/mL of dibasic sodium phosphate; at least two packets, each containing from 1 to 10 grams of a powdered flavorant including aspartame and a citrate; and at least one packet containing from 200 to 400 grams of a powdered oral rehydration mixture, the oral rehydration mixture including sodium, and a glucose containing saccharide.

These aspects may include a method for colonic cleansing using this kit, including combining the contents of at least one of the bottles of the phosphate salt laxative with at least one of the packets of the flavorant, to provide a first flavored laxative liquid; orally administering the first flavored laxative liquid; combining a portion of the oral rehydration mixture with water to provide a first oral rehydration liquid; orally administering the first oral rehydration liquid; combining the contents of at least one of the bottles of the phosphate salt laxative with at least one of the packets of the flavorant, to provide a second flavored laxative liquid; orally administering the second flavored laxative liquid; combining a portion of the oral rehydration mixture with water to provide a second oral rehydration liquid; and orally administering the second oral rehydration liquid.

In yet another aspect, the invention provides a method for colonic cleansing including combining a phosphate salt laxative and a flavorant to provide a flavored laxative liquid, orally administering to a subject the flavored laxative liquid, and orally administering to the subject an oral rehydration liquid. The flavorant includes aspartame and a citrate, and the oral rehydration liquid including sodium and a glucose containing saccharide.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

The present invention makes use of the discovery that adding a flavorant, which includes aspartame and a citrate, to a phosphate salt laxative may significantly increase the palatability of the laxative, and that administration of an oral rehydration liquid as a part of a colonic cleansing procedure with this laxative may result in improved rehydration and colonic cleansing. A better tasting pre-colonoscopy laxative may increase subject compliance with re-screening appointments. This increased compliance, combined with the improved colonic cleansing that may be achieved with an oral rehydration mixture, may reduce the need for repeat procedures attributable to inadequate colon cleansing.

Figure 1:
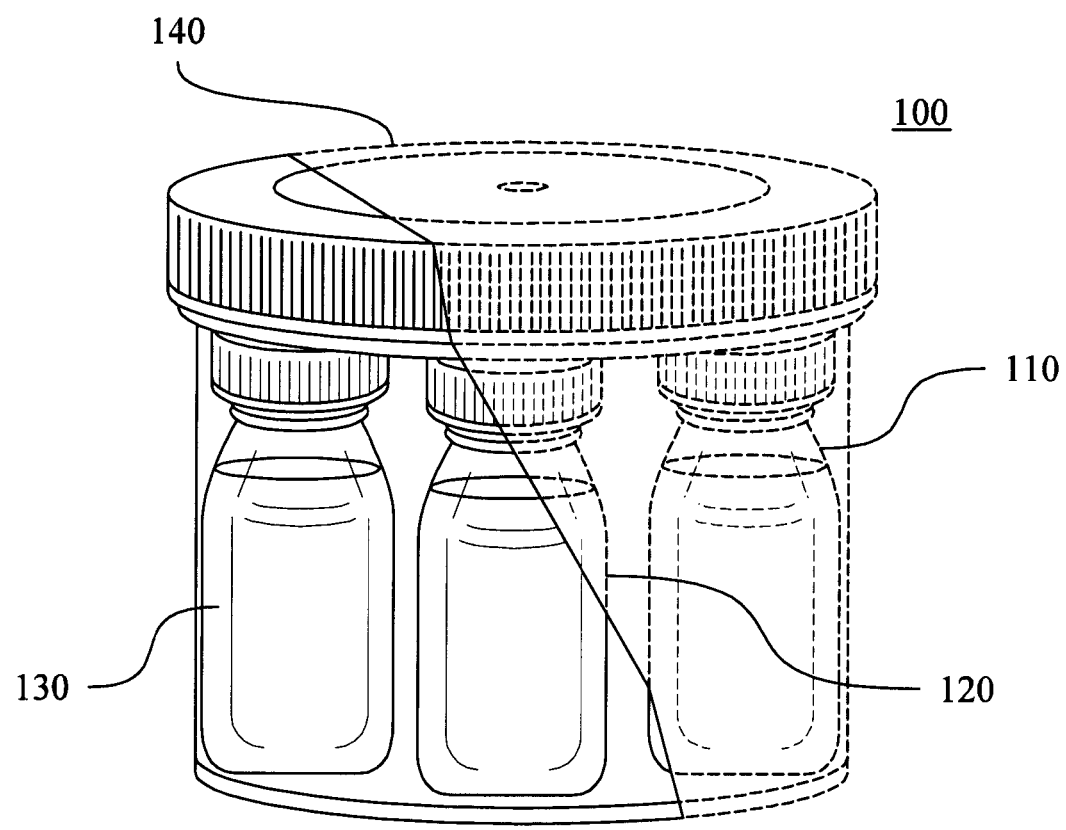
FIG. 1 is a cut-away representation of a colonic cleansing kit.

FIG. 1 represents a kit 100 for colonic cleansing including a phosphate salt laxative 110, a flavorant 120 and an oral rehydration mixture 130. The kit may also include optional exterior package 140. The kit may optionally include one or more additional items, such as a container for combining ingredients, anorectal wipes, and instructions.

The phosphate salt laxative 110 typically includes monobasic sodium phosphate (sodium dihydrogen phosphate, monohydrate —$NaH_2$—$PO_4 \cdot H_2O$) and dibasic sodium phosphate (disodium hydrogen phosphate, heptahydrate —$Na_2$—$HPO_4 \cdot 7H_2O$) in water. Phosphate salt laxatives typically have a pH from about 4.4 to about 5.2 and may be produced in multiple ways, such as by combining phosphoric acid with dibasic sodium phosphate or with caustic soda. Laxatives of this type are very stable, thus having a long shelf-life, and are considered to work in a mild and very efficient manner. An example of a phosphate salt laxative is the FLEET® PHOSPHO-SODA® liquid, available from C.B. Fleet, Lynchburg, Va. (National Formulary Monograph USP 23/NF18, p. 1430).

In one aspect, the phosphate salt laxative includes from 0.05 to 1.5 grams per milliliter (g/mL) of monobasic sodium phosphate and from 0.02 to 0.6 g/mL of dibasic sodium phosphate. In another aspect, the phosphate salt laxative includes from 0.25 to 1 g/mL or from 0.4 to 1 g/mL of monobasic sodium phosphate and from 0.1 to 0.4 g/mL or from 0.13 to 0.25 g/mL of dibasic sodium phosphate. At present, an especially preferred phosphate salt laxative includes about 0.48 g/mL of monobasic sodium phosphate and about 0.18 g/mL of dibasic sodium phosphate. Phosphate salt laxatives that include one phosphate salt, such as dibasic sodium phosphate, also may be used.

In addition to a water mixture, the phosphate salt laxative may be incorporated into a gel. For example, an aqueous liquid containing the phosphate salts may be combined with a gelling agent to form a gel. Suitable gelling agents may include gelatin, such as Gelatin, Type A, 25 Bloom, 50 mesh, from Great Lakes Gelatin, PO Box 917, Grayslake, Ill.; agar such as Sigma brand Agar A-7002 Lot 71K0093; and commercially available products that include flavorings, such as JELL-O® brand desert mix; and the like. In one aspect, about 85 grams (g) of JELL-O® may be boiled in about 130 mL of water and combined with a near boiling mixture containing 45 milliliters (mL) of FLEET® PHOSPHO-SODA® diluted with about 65 mL of water and the flavorant. Additional details regarding the incorporation of a phosphate salt laxative into a gel may be found in US. Patent Application Publication No. 2004/0071779 A1.

The phosphate salt laxative may be present in the kit as an aqueous liquid. The term "aqueous liquid" means a liquid containing water and at least one other ingredient, and includes solutions, suspensions, colloids, dispersions and slurries. The phosphate salt laxative may be present in the kit as a solid, including a powdered solid, a granulated solid, or one or more tablets. Phosphate salt laxative solids may be combined with water to form an aqueous liquid containing the phosphate salt laxative. The phosphate salt laxative may be present in the kit in one or more containers, such as bottles, tubs, sachets, envelopes, packets, tubes, ampoules, and the like. The kit may contain the phosphate salt laxative in from 1 to 10 containers, preferably in from 2 to 10 containers, more preferably in from 3 to 8 containers, more preferably in from 4 to 6 containers. Preferably the kit contains at least two containers of phosphate salt laxative, since colonic cleansing procedures may involve two separate doses of laxative. More preferably the phosphate salt laxative is present as an aqueous liquid in two or more bottles.

The flavorant 120 includes aspartame and a citrate. The citrate may include citric acid; citrate salts, such as sodium or potassium citrate; derivatives of citrate, such as citrate derivatized with ester functionality; and the like. Prior to consumption, the flavorant may be added to the phosphate salt laxative to increase its palatability. The flavorant also may include natural and/or artificial flavorings, such as natural and/or artificial fruit flavors, to further increase the palatability of the laxative. Examples of flavorants that may be combined with phosphate salt laxatives are disclosed, for example, in copending U.S. patent application Ser. No. 10/934,638, filed Sep. 3, 2004, which is incorporated herein by reference.

The flavorant may be in the form of a commercially available aspartame-based drink mixture. One such product is CRYSTAL LIGHT® powder available from Kraft Foods, Northfield, Ill. CRYSTAL LIGHT® powder includes aspartame, citric acid, and fruit flavors that result in various drink flavors when the powder is combined with water. For example, lemonade flavored CRYSTAL LIGHT® powder includes citric acid, potassium citrate, aspartame, maltodextrin, magnesium oxide, natural flavor, acesulfame potassium, lemon juice solids, artificial color, yellow 5 lake, and BHA. At present, CRYSTAL LIGHT® powder may be obtained that will make various drink flavors, including pink lemonade, lemonade, orange, tangerine-strawberry, raspberry-peach, and raspberry ice. Other drink flavors, such as raspberry lemonade, raspberry, strawberry-kiwi, strawberry-orange-banana, pineapple-orange, and grapefruit also may be used as flavorants.

Preferable compositions may include from 15 to 75 mL, from 30 to 60 mL, or from 40 to 50 mL of phosphate salt laxative in combination with from 1 to 10 g, from 2 to 6 g, or from 4 to 5 g of CRYSTAL LIGHT® drink mix. The composition also may include from 240 to 480 mL, from 300 to 420 mL, or from 270 to 450 mL of water. At present, an especially preferred composition includes about 45 mL of a phosphate salt laxative that includes about 0.48 g/mL of monobasic sodium phosphate and about 0.18 g/mL of dibasic sodium phosphate, about 4.4 g of CRYSTAL LIGHT® Pink Lemonade powder, and about 360 mL of water.

In another aspect, the flavorant may be in the form of a reduced-filler aspartame-based mixture. In relation to a commercially available aspartame-based drink mixture, such as CRYSTAL LIGHT®, a reduced-filler aspartame-based mixture has a reduced amount of maltodextrin. Preferably, the reduced-filler mixture also contains less natural flavoring and flowability enhancers than commercially available drink mixtures. By reducing the amount of maltodextrin, natural flavoring, and the like, the amount of flavorant added to increase the palatability of the phosphate salt laxative may be reduced. A preferable reduced-filler flavorant includes aspartame, citrates, artificial lemon flavoring, and plant extract. At present, an especially preferred plant extract for use in a reduced-filler flavorant is available from WILD Flavors, Inc., Erlanger, Ky. and is referred to as RESOLVER®. It is believed that the plant extracts in RESOLVER® occupy the receptors on the tongue that are responsible for bitter tastes, thus neutralizing the otherwise bitter aspects of the flavorant and/or the phosphate salt laxative.

Preferable compositions may include from 1 to 3 g, preferably about 2 g of a reduced-filler aspartame-based mixture in combination with from 40 to 50 mL of a phosphate salt laxative. At present, an especially preferred composition includes about 45 mL of a phosphate salt laxative that includes about 0.48 g/mL of monobasic sodium phosphate and about 0.18 g/mL of dibasic sodium phosphate, 2.0 g+/− 10% by weight of the reduced-filler aspartame-based mixture, and about 360 mL of water.

The flavorant may be present in a kit as an aqueous liquid. The flavorant may be present in a kit as a solid, including a powdered solid, a granulated solid, or one or more tablets. The flavorant may be present in the kit in one or more containers, such as bottles, tubs, sachets, envelopes, packets, tubes, ampoules, and the like. Preferably the kit includes at least two containers of flavorant. More preferably the kit includes two containers of flavorant, each container having an amount of flavorant appropriate to combine with a single dose of phosphate salt laxative. Preferably the flavorant is present as a powder contained in two packets, each packet corresponding to a dose of phosphate salt laxative.

The kit also may include ascorbic acid or a salt thereof. Due to the poor stability of ascorbic acid in solution, the ascorbic acid may be separately packaged and added to the phosphate salt laxative before use. In a preferred aspect, when the flavorant is packaged as a dry powder, the ascorbic acid may be packaged as a dry powder with the flavorant. When packaged as a dry powder, such as with the flavorant, the ascorbic acid may be coated to improve its stability. Suitable coatings include silicone, ethyl cellulose, and the like. In one aspect, enough ascorbic acid is added to provide a pre-administration solution concentration of from 0.25 to 50 grams/liter (g/L) or from 1 to 25 g/L. Additional details regarding the use of ascorbic acid in laxative preparations may be found in U.S. Pat. No. 5,274,001.

The oral rehydration mixture 130 contains sodium and a glucose containing saccharide. Sodium may be present in the mixture as a salt. Examples of sodium salts include sodium chloride, sodium phosphate, and sodium citrate. Preferably, the salt has a solubility in water at room temperature of at least one gram per liter. The term "glucose containing saccharide" means either glucose, or a saccharide that can be hydrolyzed to form a composition containing glucose.

Saccharides are polyhydroxy aldehydes or ketones, and include monosaccharides, disaccharides, oligosaccharides, and polysaccharides. Saccharides typically have a water solubility of at least one gram per liter. Examples of glucose containing saccharides include glucose, sucrose, lactose, maltose, amylose, glycogen and maltodextrin. A variety of glucose containing saccharides may be present in the oral rehydration mixture, as may other saccharides that do not contain glucose. Examples of saccharides that do not contain glucose include fructose, galactose, allose, altrose, mannose, gulose, idose, talose, ribose, arabinose, lyxose, ribose, xylose, erythrose, and threose. As used herein, reference to any saccharide by a single name also includes all forms of that saccharide which may be in equilibrium with the specific saccharide named, in aqueous mixture at room temperature. For example, the term "glucose" includes glucose and all 5- and 6-membered cyclic hemiacetals in equilibrium with glucose in aqueous mixture at room temperature.

An oral rehydration mixture may contain other ingredients, such as proteins, amino acids, polylactate, and salts such as potassium, magnesium and calcium salts. An oral rehydration mixture may contain a variety of excipients and/or additives, for example, flavoring agents, coloring agents, carbonates, viscosity modifiers, preservatives, and the like. Examples of flavoring agents include anise oil, cinnamon oil, vanilla, vanillin, cocoa, chocolate, menthol, grape, peppermint oil, oil of wintergreen, clove oil, bay oil, anise oil, eucalyptus, thyme oil, cedar leaf oil, oil of nutmeg, oil of sage, oil of bitter almonds, cassia oil, citric acid, citrus oils such as lemon, orange, lime and grapefruit oils, and fruit essences, including apple, pear, peach, berry, wildberry, date, blueberry, kiwi, strawberry, raspberry, cherry, plum, pineapple, and apricot. Examples of coloring agents include FD&C Red No. 3, FD&C Red No. 20, FD&C Yellow No. 6, FD&C Blue No. 2, D&C Green No. 5, FD&C Orange No. 5, D&C Red No. 8, caramel, ferric oxide, pigments, dyes, tints, titanium dioxide, grape skin extract, beet red powder, beta carotene, annato, carmine, turmeric, and paprika.

Examples of oral rehydration mixtures and oral rehydration liquids include GATORADE® Thirst Quencher, GATORADE® Endurance Formula, GATORADE® Endurance Series, and PROPEL® Fitness Water (PepsiCo, Inc.; Purchase, N.Y.). Examples of oral rehydration mixtures and oral rehydration liquids include ACCELERADE (PacificHealth Laboratories, Inc.; Matawan, N.J.); ALL SPORT BODY QUENCHER® (Monarch Beverage Company; Atlanta, Ga.); CYTOMAX sports drink (CytoSport; Benicia, Calif.); $GU_2O$ sports drink (GU Sports; Berkeley, Calif.); and POWERADE® (The Coca-Cola Company; Atlanta, Ga.). Examples of oral rehydration mixtures and oral rehydration liquids include OralSuero, Sueroral Hiposódico, and Sueroral Casen (Casen Fleet; Madrid, Spain). Examples of oral rehydration mixtures and oral rehydration liquids include PEDIALYTE® oral rehydration solutions (Ross Products; Columbus, Ohio).

An oral rehydration mixture preferably contains a ratio of glucose containing saccharide:sodium of 0.1 to 15 g:0.1 to 200 millimole (mmol), more preferably 1 to 10 g:2 to 100 mmol, more preferably 5 to 7 g:10 to 30 mmol. Preferably the oral rehydration mixture is administered as an oral rehydration liquid, which is a mixture of the oral rehydration mixture ingredients with water. An oral rehydration liquid preferably contains from 0.1 to 15% (w/v) of saccharide, more preferably from 1 to 10% (w/v) saccharide, and more preferably from 5 to 7% (w/v) saccharide. Preferably, an oral rehydration liquid contains from 0.1 to 200 millimole per liter (mmol/L) of sodium, more preferably from 2 to 100 mmol/L sodium, and more preferably from 10 to 30 mmol/L sodium.

The oral rehydration mixture may be present in the kit as an oral rehydration liquid. The oral rehydration mixture may be present in the kit as a solid, including a powdered solid, a granulated solid, or one or more tablets. The oral rehydration mixture may be present in the kit in one or more containers, such as bottles, tubs, sachets, packets, envelopes, tubes, ampoules, and the like. For example, the kit may include one or more packets containing oral rehydration mixture solids. In another example, the kit may include one or more containers of oral rehydration liquid. The kit may contain two containers of oral rehydration mixture or of oral rehydration liquid, to correspond to two doses of the phosphate salt laxative.

One or more containers for combining ingredients optionally may be present in a kit. A container may be present in the kit in the form of a cup, a bottle, a vial, a tube, or the like, which may be formed in part or in whole from plastic, glass, paper, STYROFOAM®, and the like. A container may be equipped with a fully or partially detachable lid that initially may be part of the container or may be affixed to the container by mechanical, adhesive, or other means. Preferably the kit contains one or more cups, and more preferably contains one or more plastic cups.

One or more anorectal wipes optionally may be present in the kit. Anorectal wipes may be made from any suitable substrate, such as cloth, paper, or combinations thereof, and may be wetted with an aqueous mixture that may include one or more active ingredients. Examples of active ingredients include a local anesthetic such as pramoxine hydrochloride, and a protectant such as glycerin. The aqueous mixture also may include one or more inactive ingredients, such as cetylpyridinium chloride, citric acid, disodium EDTA, eucalyptol, menthol, octoxynol-9, sodium benzoate, and sodium citrate. The anorectal wipes may be in the form of pads and the like, such as FLEET® Pain-Relief Pre-Moistened anorectal pads. In one aspect, four individually wrapped wipes are preferred. The anorectal wipes may be rectangular in shape, having dimensions of about 4 cm by about 7 cm. The anorectal wipes may be present in the kit in one or more containers, such as bottles, tubs, sachets, envelopes, packets, tubes, and the like. For example, the kit may include two packets containing one or more anorectal wipes each. Preferably the kit includes two anorectal wipes packets, each packet containing two anorectal wipes.

Instructions may optionally be present in the kit. Instructions may include directions regarding how to combine the phosphate salt laxative with the flavorant to form the colonic cleansing composition, regarding when to consume the colonic cleansing composition in relation to the time of a colonoscopy procedure, regarding when to consume the oral rehydration mixture, and how to apply the anorectal wipes to provide the desired soothing effect. The instructions may be present in a variety of forms, including one or more printed sheets, printing on the outside or inside the exterior package, writing incorporated on one or more of the containers enclosed in the exterior package, a CD-ROM, a DVD-ROM, a uniform resource locator (URL) for a website, and the like.

The optional exterior package 140 may be sized and configured to contain one or more other components of the kit. An exterior package may be a cup, a bottle, a vial, a tube, or the like, which may be formed in part or in whole from plastic, glass, paper, STYROFOAM®, and the like. An exterior package may be equipped with a fully or partially detachable lid that initially may be part of the container or may be affixed to the container by mechanical, adhesive, or other means.

The optional exterior package may include one or more supporting structures, such as walls, wells, movable or removable trays, etc., so as to segregate the various components. In one example, a kit that includes two doses each of phosphate salt laxative, flavorant, and oral rehydration mixture may include an exterior package having a single wall that partitions the package into two regions, with the components intended for use in each dose segregated between the two regions. In another example, an exterior package may include walls and/or wells that allow the individual components to be segregated, such that all the containers of phosphate salt laxative are placed together, all the containers of flavorant are placed together, and all the containers of oral rehydration mixture are placed together. Supporting structures may be formed in part or in whole from plastic, glass, paper, STYROFOAM®, and the like. An example of an exterior container that includes supporting structures is disclosed in U.S. Patent Application Publication No. 2005/0061861 A1.

Figure 2:
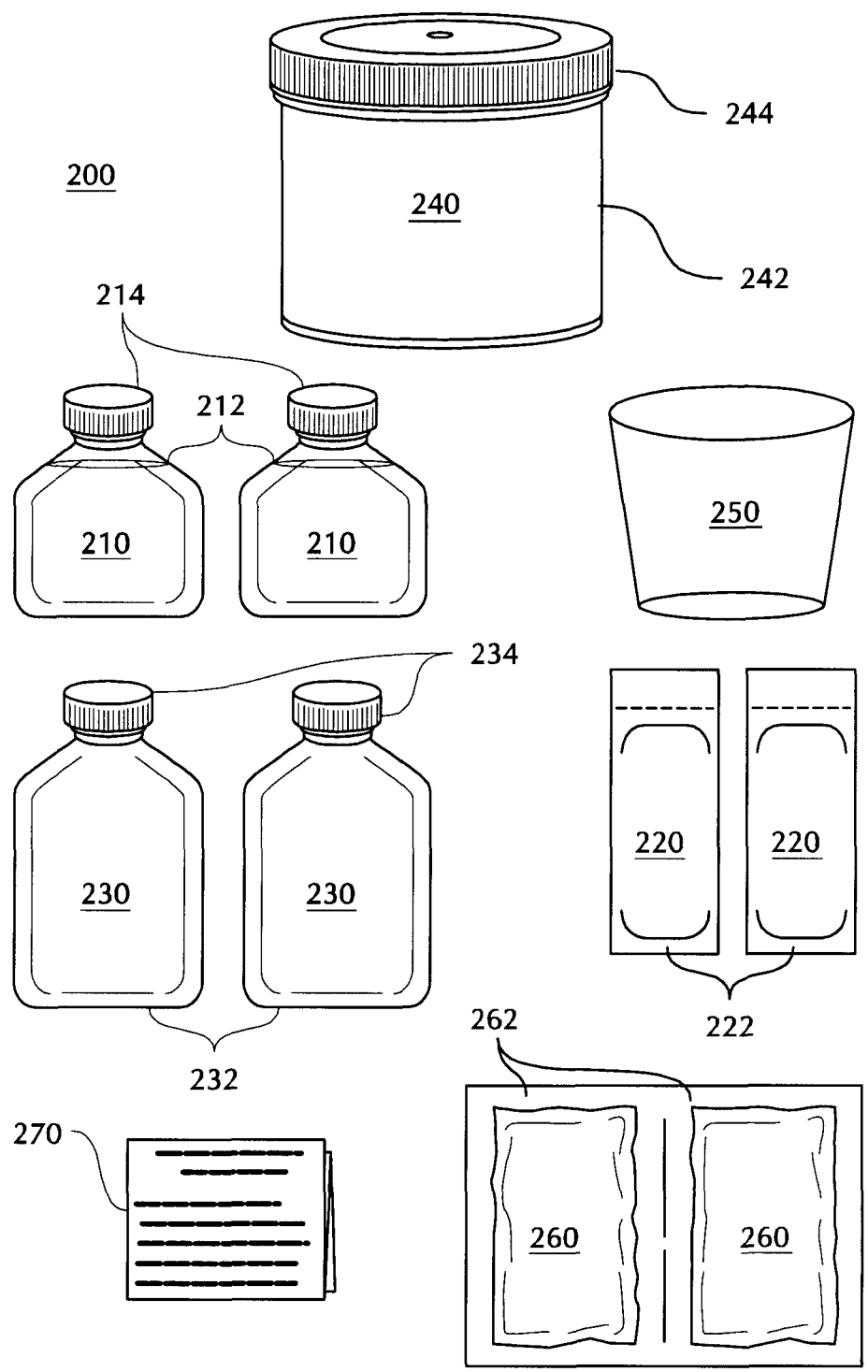
FIG. 2 is a representation of individual components that may be found in a colonic cleansing kit.

FIG. 2 represents a kit 200 for colonic cleansing including a phosphate salt laxative 210, a flavorant 220, an oral rehydration mixture 230, an exterior package 240, a container for combining ingredients 250, anorectal wipes 260, and instructions 270. The phosphate salt laxative and the oral rehydration mixture are each depicted as aqueous liquids, in plastic bottles 212 and 232 having screw-top lids 214 and 234. The flavorant, in powder form, and the anorectal wipes are depicted as enclosed in packets 222 and 262, respectively, such as packets made from foil-lined paper. The exterior package is depicted as a plastic jar 242 having a removable screw-type lid 244.

In one example, each laxative bottle may contain about 45 mL of phosphate salt laxative, and each oral rehydration mixture bottle may contain about 1.5 to 2 liters of oral rehydration liquid. The flavorant packets may be rectangular, each packet having a width of about 4.1 to about 4.4 centimeters (cm) and a length of about 6.3 to about 7.6 cm, and each packet containing about 4 to 5 g flavorant. The anorectal wipe packets may be rectangular, each packet having a width of about 4 to about 6 cm and a length of about 7 to about 9 cm, and each packet containing two wipes.

Figure 3:
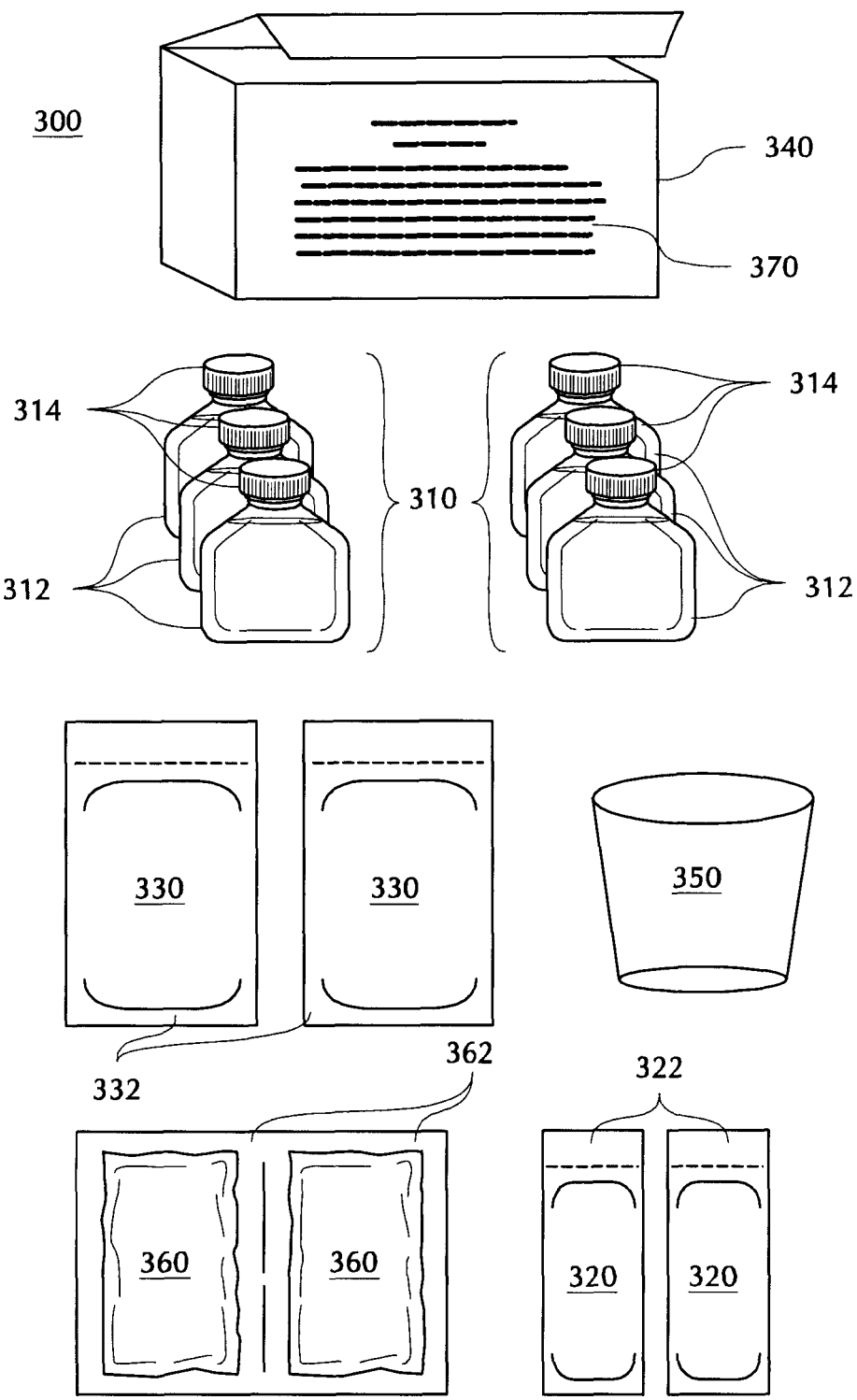
FIG. 3 is a representation of individual components that may be found in a colonic cleansing kit.

FIG. 3 represents a kit 300 for colonic cleansing including a phosphate salt laxative 310, a flavorant 320, an oral rehydration mixture 330, an exterior package 340, a container for combining ingredients 350, and anorectal wipes 360. The phosphate salt laxative is depicted as an aqueous liquid in six plastic bottles 312 having screw-top lids 314. The flavorant, the oral rehydration mixture (each in powder form) and the anorectal wipes are depicted as enclosed in packets 322, 332 and 362, respectively, such as packets made from foil-lined paper. The exterior package is depicted as a box having instructions 370 printed on the box.

In one example, each bottle contains about 15 mL of phosphate salt laxative. The flavorant packets, oral rehydration mixture packets, and anorectal wipe packets may be rectangular in shape. The oral rehydration mixture packet may be rectangular, having a width of about 5 to about 12 cm and a length of about 5 to about 12 cm, and containing from 8 to 10 g oral rehydration mixture powder. The flavorant packets may be rectangular, each packet having a width of about 4.1 to about 4.4 centimeters (cm) and a length of about 6.3 to about 7.6 cm, and each packet containing about 4 to 5 g flavorant. The anorectal wipe packets may be rectangular, each packet having a width of about 4 to about 6 cm and a length of about 7 to about 9 cm, and each packet containing two wipes.

Figure 4:
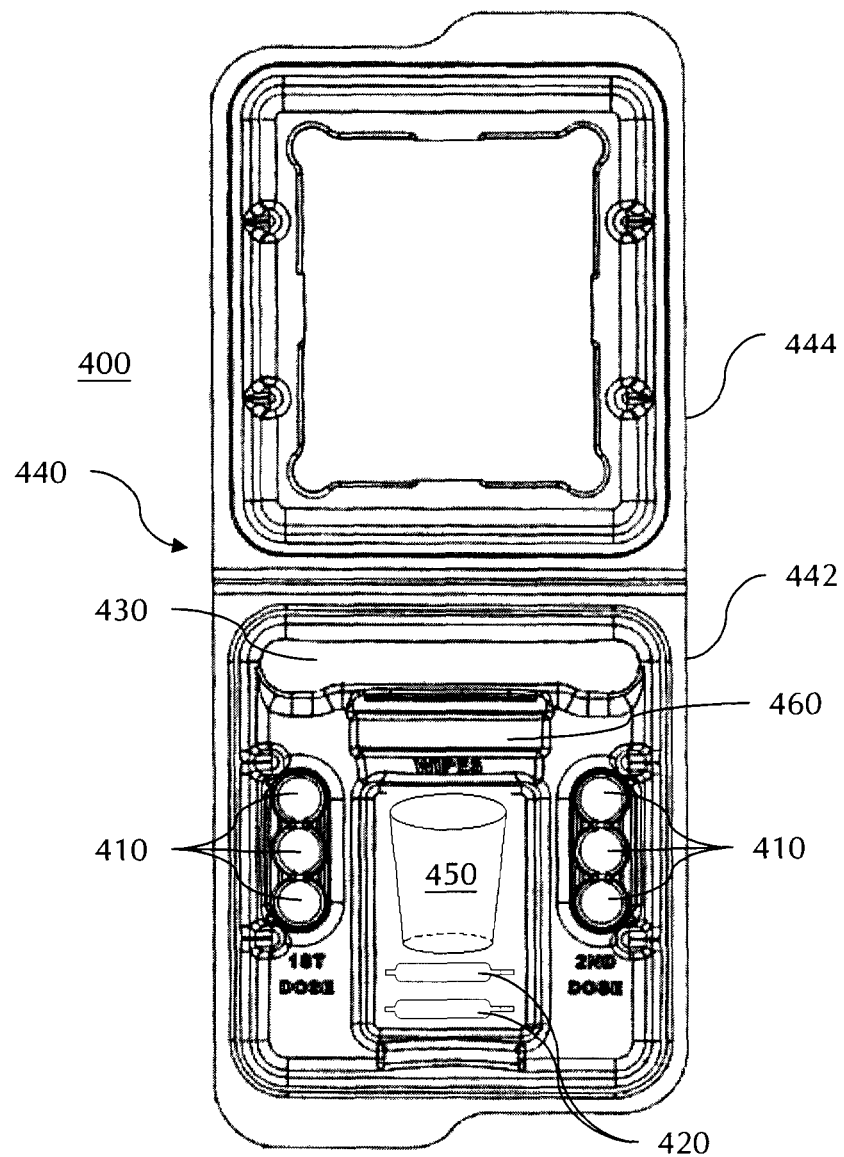
FIG. 4 is a representation of a colonic cleansing kit.

FIG. 4 represents a kit 400 for colonic cleansing including phosphate salt laxative 410, flavorant 420, oral rehydration mixture 430, an exterior package 440, a container for combining ingredients 450, and anorectal wipes 460. The phosphate salt laxative is depicted as an aqueous liquid in six bottles. The oral rehydration mixture, the flavorant (each in powder form) and the anorectal wipes are depicted as enclosed in packets, such as packets made from foil-lined paper. The exterior package is depicted as a clam-shell package having a tray 442 and a cover 444 pivotally attached to the tray.

Figure 5A:
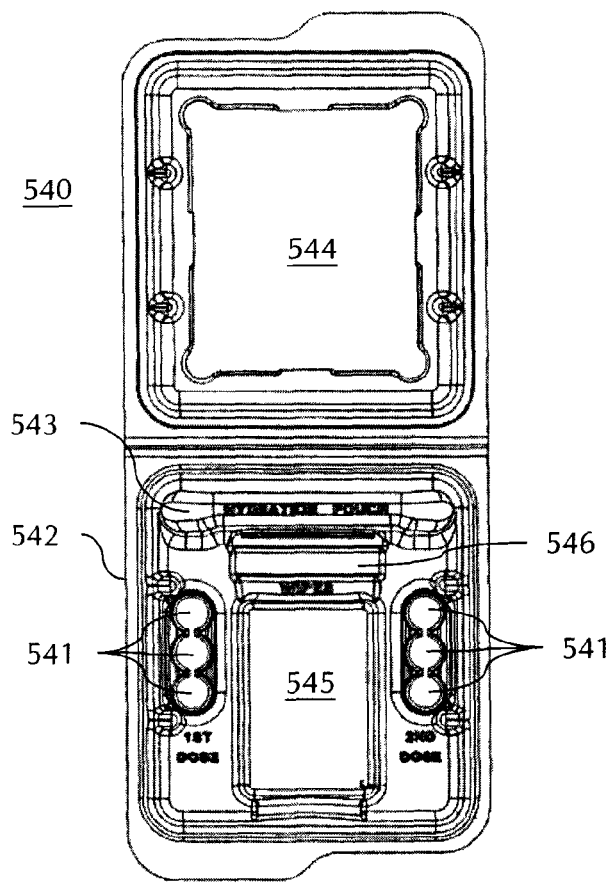
FIG. 5A is a top view representation of an open exterior package.
Figure 5B:
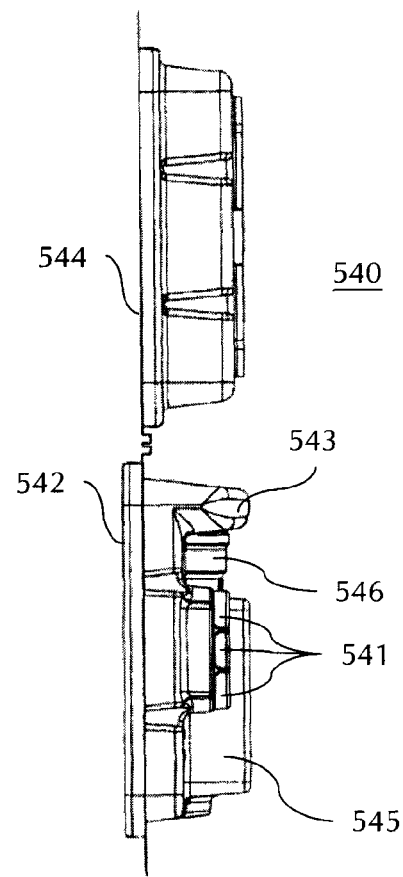
FIG. 5B is a side view representation of an open exterior package.
Figure 5C:
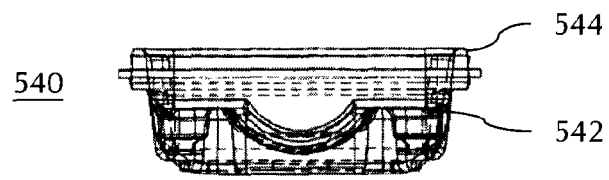
FIG. 5C is a front view representation of a closed exterior package.

FIGS. 5A-5C represent an exterior package 540 similar to exterior package 440 of FIG. 4. The package 540 includes a tray 542, a cover 544 pivotally attached to the tray, six wells 541 for bottles of phosphate salt laxative, a well 543 for one or more containers of oral rehydration mixture, a well 545 for one or more containers of flavorant and optionally for one or more containers for combining ingredients, and a well 546 for anorectal wipes. FIG. 5A is a top view representation of the open package, FIG. 5B is a side view representation of the open package, and FIG. 5C is a front view representation of the closed package.

A method for colonic cleansing may include orally administering to a subject a flavored laxative liquid, and orally administering to the subject an oral rehydration liquid. The flavored laxative liquid contains a phosphate salt laxative and a flavorant containing aspartame and a citrate. The oral rehydration liquid contains water, sodium and a glucose containing saccharide. By orally administering the flavored laxative liquid and the oral rehydration liquid, the colon may be cleansed.

Orally administering a flavored laxative liquid may include combining the phosphate salt laxative and the flavorant. The phosphate salt laxative and the flavorant independently may be solid or may be in an aqueous liquid, and the solid(s) and/or liquid(s) may be combined to form the flavored laxative liquid. Water may also be added to the phosphate salt laxative and/or the flavorant, regardless of whether one or both components are already in the form of an aqueous liquid. In one example, an aqueous phosphate salt laxative is combined with a powdered flavorant and water to provide the flavored laxative liquid. In this example, the flavorant may include a gelling agent, such that the flavored laxative may be administered in the form of a gel.

Preferably the flavored laxative liquid is administered so that from 0.4 to 0.85 g of monobasic sodium phosphate and from 0.1 to 0.5 g of dibasic sodium phosphate are consumed per kilogram of body weight of the subject. In one example, about 45 mL of a phosphate salt laxative, including about 0.48 g/mL of monobasic sodium phosphate and about 0.18 g/mL of dibasic sodium phosphate, is mixed with about 4.4 g of CRYSTAL LIGHT® Pink Lemonade powder, and about 360 mL of water. In another example, about 45 mL of a phosphate salt laxative, including about 0.48 g/mL of monobasic sodium phosphate and about 0.18 g/mL of dibasic sodium phosphate, is mixed with about 2.0 g of a reduced-filler aspartame-based mixture, and about 360 mL of water.

Orally administering to the subject an oral rehydration liquid may include combining an oral rehydration mixture and water, to form the oral rehydration liquid. In one example, from 0.5 to 5 liters of oral rehydration liquid is administered. Preferably the oral rehydration liquid is orally administered, at least in part after administration of the flavored laxative liquid, and before colonic cleansing is complete. However, it is still expected to be effective if administration of the oral rehydration liquid is within a few hours prior to oral administration of the flavored laxative liquid. Of the fluids orally administered from 4 hours before to 24 hours after oral administration of the flavored laxative liquid, preferably at least 50% of the fluids are in the form of an oral rehydration liquid. More preferably at least 75% of the fluids are in the form of an oral rehydration liquid, and more preferably at least 90% of the fluids are in the form of an oral rehydration liquid.

A method for colonic cleansing may be carried out in two separate steps. For example, a method for colonic cleansing may include orally administering to a subject a first aqueous liquid containing the phosphate salt laxative and the flavorant, orally administering to the subject a first oral rehydration liquid, orally administering to the subject a second aqueous liquid containing the phosphate salt laxative and the flavorant, and orally administering to the subject a second oral rehydration liquid. The compositions of the first and second aqueous liquids may be the same or different, and the compositions of the first and second oral rehydration liquids may be the same or different. Preferably the administration of the first aqueous liquid and the first oral rehydration liquid are performed about 14 hours prior to a colonoscopy, and the administration of the second aqueous liquid and the second oral rehydration liquid are performed about 3 hours prior to the colonoscopy.

A method for colonic cleansing using a kit may include combining a phosphate salt laxative with a flavorant to provide a flavored laxative liquid, orally administering to a subject the flavored laxative liquid, and orally administering to the subject an oral rehydration liquid. In one example, a method for colonic cleansing using kit 100 includes combining the phosphate salt laxative 110 with the flavorant 120 to provide a flavored laxative liquid, orally administering to a subject the flavored laxative liquid, and orally administering to the subject the oral rehydration liquid 130. This method may be carried out in two separate steps. For example, orally administering the flavored laxative liquid may include orally administering a first portion of the flavored laxative liquid, and orally administering a second portion of the flavored laxative liquid; and orally administering the oral rehydration liquid 130 may include orally administering a first portion of the oral rehydration liquid, and orally administering a second portion of the oral rehydration liquid. In this example, the first portion of the oral rehydration liquid is administered prior to the administration of the second portion of the flavored laxative liquid.

In another example, a method for colonic cleansing using kit 200 includes combining the contents of one phosphate salt laxative bottle 212 with the contents of one flavorant packet 220 in the container 250 to provide a first flavored laxative liquid, orally administering the first flavored laxative liquid, orally administering the contents of one oral rehydration liquid bottle 232, combining the contents of the other phosphate salt laxative bottle 212 with the contents of the other flavorant packet 220 in the container 250 to provide a second flavored laxative liquid, orally administering the second flavored laxative liquid, and orally administering the contents of the other oral rehydration liquid bottle 232. Combining the contents of a phosphate salt laxative bottle 212 with the contents of a flavorant packet 220 in the container 250 may include adding additional water to the mixture.

In another example, a method for colonic cleansing using kit 300 includes combining the contents of one, two or three phosphate salt laxative bottles 312 with at least a portion of the contents of one flavorant packet 320 in the container 350 to provide a first flavored laxative liquid; orally administering the first flavored laxative liquid; combining at least a portion of the contents of one oral rehydration mixture packet 332 with water to provide a first oral rehydration liquid; orally administering the first oral rehydration liquid; combining the contents of one, two or three of the other phosphate salt laxative bottles 312 with at least a portion of the contents of the other flavorant packet 320 in the container 350 to provide a second flavored laxative liquid; orally administering the second flavored laxative liquid; combining at least a portion of the contents of the other oral rehydration mixture packet 332 with water to provide a second oral rehydration liquid; and orally administering the second oral rehydration liquid.

Combining the contents of one, two or three phosphate salt laxative bottles 312 with at least a portion of the contents of a flavorant packet 320 in the container 350 may include adding additional water to the mixture. This method may be used to facilitate the use of variable doses of the flavored laxative liquid. For example, a subject may be administered small doses containing one bottle each of the phosphate salt laxative if the body weight of the subject is below a lower threshold value, and a subject may be administered large doses containing three bottles each of the phosphate salt laxative if the body weight of the subject is above an upper threshold value. An entire packet of flavorant may be combined with the phosphate salt laxative, or a smaller amount of the flavorant may be used to suit the taste of the subject. The oral rehydration mixture may be combined with water in the container 350, or it may be combined with water in a different container.

In another example, a method for colonic cleansing using kit 400 includes combining the contents of one, two or three bottles of phosphate salt laxative 410 with at least a portion of the contents of one packet of flavorant 420 in the container 450 to provide a first flavored laxative liquid; orally administering the first flavored laxative liquid; combining a portion of the contents of the packet of oral rehydration mixture 430 with water to provide a first oral rehydration liquid; orally administering the first oral rehydration liquid; combining the contents of one, two or three of the other bottles of phosphate salt laxative 410 with at least a portion of the contents of the other packet of flavorant 420 in the container 450 to provide a second flavored laxative liquid; orally administering the second flavored laxative liquid; combining at least a portion of the remaining contents of the packet of oral rehydration mixture 430 with water to provide a second oral rehydration liquid; and orally administering the second oral rehydration liquid. This method may be used to facilitate the use of variable doses of the flavored laxative liquid.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A kit for colonic cleansing, comprising:
   a phosphate salt laxative, comprising from 0.4 to 1 gram/mL of monobasic sodium phosphate and from 0.13 to 0.25 gram/mL of dibasic sodium phosphate;
   a flavorant, comprising aspartame, maltodextrin, acesulfame potassium and a citrate, wherein about 45 mL of the phosphate salt laxative is present for each 2-6 grams of the flavorant, and
   an oral rehydration mixture, comprising sodium, and a glucose containing saccharide.

2. The kit of claim 1, where the phosphate salt laxative comprises 0.48 gram/mL of monobasic sodium phosphate and 0.18 gram/mL of dibasic sodium phosphate.

3. The kit of claim 1, where the phosphate salt laxative is present as a solid.

4. The kit of claim 1, where the phosphate salt laxative is present as an aqueous liquid in at least one bottle.

5. The kit of claim 4, where the phosphate salt laxative is present as an aqueous liquid in at least two bottles, each bottle comprising from 10 to 75 mL of the liquid.

6. The kit of claim 4, where the phosphate salt laxative is present as an aqueous liquid in at least six bottles, each bottle comprising from 10 to 75 mL of the liquid.

7. The kit of claim 1, where the flavorant further comprises a flavoring selected from the group consisting of natural fruit flavors, artificial fruit flavors, and combinations thereof.

8. The kit of claim 1, where the citrate comprises citric acid and potassium citrate; and the flavorant further comprises natural flavor, lemon juice solids, and artificial color.

9. The kit of claim 1, where the flavorant further comprises ascorbic acid or a salt thereof.

10. The kit of claim 1, where the flavorant is present as an aqueous liquid.

11. The kit of claim 1, where the flavorant is present as a solid.

12. The kit of claim 11, where the flavorant is present as a powder in at least one packet.

13. The kit of claim 12, where the flavorant is present as a powder in at least two packets, each packet comprising from 1 to 10 grams of the powder.

14. The kit of claim 1, where the oral rehydration mixture comprises a ratio of glucose containing saccharide to sodium of 0.1 to 15 g:0.1 to 200 mmol.

15. The kit of claim 1, where the oral rehydration mixture comprises a ratio of glucose containing saccharide to sodium of 1 to 10 g:2 to 100 mmol.

16. A method for colonic cleansing using the kit of claim 1, comprising:
   combining the phosphate salt laxative and the flavorant to provide a flavored laxative liquid;
   orally administering to a subject the flavored laxative liquid; and
   orally administering to the subject an oral rehydration liquid,
   the oral rehydration liquid comprising sodium and a glucose containing saccharide.

17. A kit for colonic cleansing, comprising:
   at least two bottles, each comprising about 45 mL of a phosphate salt laxative, the phosphate salt laxative comprising
   water,
   from 0.4 to 1 gram/mL of monobasic sodium phosphate, and
   from 0.13 to 0.25 gram/mL of dibasic sodium phosphate
   at least two packets, each comprising from 2-6 grams of a powdered flavorant, the flavorant comprising
   aspartame, maltodextrin, acesulfame potassium and a citrate, wherein about 45 mL of the phosphate salt laxative is present for each 2-6 grams of the flavorant, and at least one packet comprising from 200 to 400 grams of a powdered oral rehydration mixture, the oral rehydration mixture comprising sodium, and a glucose containing saccharide.

* * * * *